(12) United States Patent  (10) Patent No.: US 7,857,757 B2
Schaaf  (45) Date of Patent: Dec. 28, 2010

(54) ENDOSCOPE WITH A FLEXIBLE PROBE

(75) Inventor: Hansgeorg Schaaf, Reichertshausen (DE)

(73) Assignee: Polydiagnost GmbH, Pfaffenhofen (DE)

( * ) Notice: Subject to any disclaimer, the term of this patent is extended or adjusted under 35 U.S.C. 154(b) by 1283 days.

(21) Appl. No.: 11/409,039

(22) Filed: Apr. 24, 2006

(65) Prior Publication Data

US 2006/0264919 A1 Nov. 23, 2006

(30) Foreign Application Priority Data

Apr. 22, 2005 (DE) .................... 10 2005 018 825

(51) Int. Cl.
*A61B 1/06* (2006.01)
(52) U.S. Cl. ........................................ 600/182
(58) Field of Classification Search .............. None
See application file for complete search history.

(56) References Cited

U.S. PATENT DOCUMENTS

| | | | | |
|---|---|---|---|---|
| 2,975,785 A | * | 3/1961 | Sheldon et al. | 600/141 |
| 4,762,120 A | | 8/1988 | Hussein | |
| 4,813,400 A | * | 3/1989 | Washizuka et al. | 600/161 |
| 5,152,277 A | * | 10/1992 | Honda et al. | 600/116 |
| 5,396,880 A | * | 3/1995 | Kagan et al. | 600/109 |
| 5,569,161 A | | 10/1996 | Ebling et al. | |
| 6,006,002 A | * | 12/1999 | Motoki et al. | 385/117 |
| 6,148,227 A | | 11/2000 | Wagnières | |
| 6,374,025 B1 | * | 4/2002 | Iriyama et al. | 385/117 |
| 2002/0147383 A1 | | 10/2002 | Weber et al. | |
| 2002/0166780 A1 | * | 11/2002 | Bautista et al. | 206/303 |
| 2005/0192479 A1 | * | 9/2005 | Forster et al. | 600/182 |

FOREIGN PATENT DOCUMENTS

| | | |
|---|---|---|
| DE | 198 00 312 A1 | 7/1999 |
| DE | 199 28 272 A1 | 1/2001 |
| DE | 199 56 516 A1 | 6/2001 |
| DE | 199 55 614 C1 | 7/2001 |
| DE | 201 18 886 U1 | 3/2002 |
| DE | 100 45 036 C1 | 7/2002 |
| DE | 101 07 156 A1 | 9/2002 |
| DE | 101 16 859 A1 | 11/2002 |
| DE | 102 41 946 A1 | 3/2003 |
| FR | 2834348 A | 7/2003 |

* cited by examiner

*Primary Examiner*—Philip R Smith
(74) *Attorney, Agent, or Firm*—Crowell & Moring LLP

(57) ABSTRACT

An endoscope with a flexible, multi-lumen catheter probe 1, a grip 3 provided at the proximal end of the probe, a control element 13 attached to the distal end of the probe and movably guided in the axial direction on catheter probe 1, wherein the catheter probe 1 is to be connected non-rotatingly to the grip 3 by means of a releasable lock 2, the distal end of the optical lumen 4 has a transparent seal 5, and optical system 6 is displaceably disposed inside optic lumen 4 and can be removed from optic lumen 4.

12 Claims, 3 Drawing Sheets

ENDOSCOPE WITH A FLEXIBLE PROBE

BACKGROUND AND SUMMARY OF THE INVENTION

Figure 1:
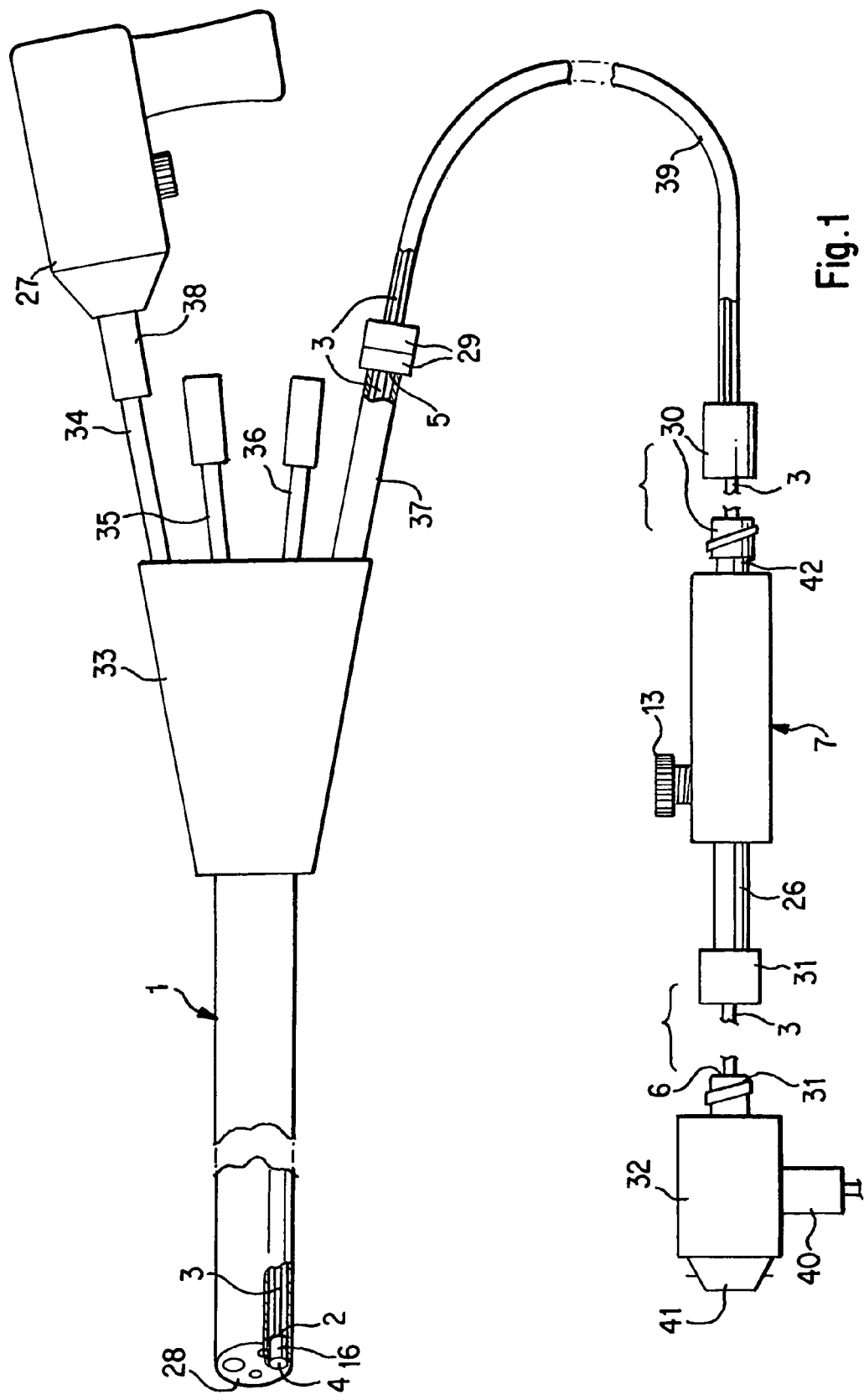

This application claims the priority of German Application No. 10 2005 018 825.7 filed Apr. 22, 2005, the disclosure of which is expressly incorporated by reference herein.

An endoscope of that kind which is known from U.S. Pat. No. 5,569,161 includes in the catheter probe an optical lumen in which is provided an optical strand with optical fibers extending in the longitudinal direction of the catheter. The distal opening of the optical lumen is closed by a transparent cover. Provided between the proximal end of the optical lumen and the proximal end of the optical strand is a length compensating device which has a resilient action and with which the distal end of the optical strand is held in a condition of bearing against the transparent cover. With an endoscope of that kind there is no need to sterilise the optical strand between individual uses as, during the patient treatment, the optical strand is hermetically separated off with respect to the interior of the body by the components of the endoscope, in particular by the distal cover at the optical lumen and the catheter probe.

In the case of endoscopes as are known for example from DE 100 45 036 C1 the distal end of the probe can be angled by means of a control element, for example a pulling wire or pulling cable, and can possibly be bent back through 180° with respect to the axis of the catheter probe. In that situation and also in the movement out of the bent position back into the position of the distal end of the probe, in which it is aligned in the longitudinal direction, relatively great changes occur in the force with which the distal end of the optical strand bears against the cover, even when using a length compensating device. In addition the distal end of the optical strand can also be moved away from the cover. That results in a constriction of the angle of view and thus the viewing region which is observed by way of the optical strand. On the other hand the contact forces exerted against the cover can become so great that there is the risk of the cover becoming detached from the distal end of the optical lumen.

The object of the invention is to provide an endoscope of the kind set forth in the opening part of this specification, in which in all operating conditions of the endoscope and in particular the cathode probe which occur in practice, the distal end of the optical strand is guaranteed to bear satisfactorily against the distal lumen cover.

In accordance with the invention that object is attained by the features of claim 1 and in particular by the features of claim 11.

In the invention the length compensating device includes a force storage means, preferably in the form of a spring, in particular a compression spring. The spring engages two force application locations of which the one force application location is rigidly connected to the proximal end of the optical strand and the other force application location is rigidly connected to the proximal end of the optical lumen. In normal endoscope operation, oppositely acting forces are applied to the force application location, such forces resulting in a given contact force with which the distal end of the optical strand is caused to bear in contact against the transparent cover of the optical lumen. In order to prevent damage to the cover and the distal end of the optical strand, the force is limited to low values, for example of the order of magnitude of 2 N. The length compensating effect to be achieved when flexing the catheter probe, which results in a change in the spacing between the two force application locations, is therefore possible only within close limits while maintaining the required contacting relationship of the distal end of the optical strand against the cover. That means that the possible motions and in particular the degree of bending in the distal region of the catheter probe are limited.

With the present invention, the extent of the possible movement and in particular the degree of possible bending of the distal end of the catheter probe is increased to 180° with respect to the probe axis and therebeyond, in which respect the distal end of the optical strand is still guaranteed to satisfactorily bear in contact against the transparent cover of the optical lumen.

For that purpose the spacing of the force application location of the length compensating device, that location being connected to the proximal end of the optical strand, from the proximal end of the optical strand, can be altered. A further possibility provides that the spacing of the force application location of the length compensating device, which is rigidly connected to the proximal end of the optical lumen, can be displaced with respect to the proximal optical lumen. It is also possible for both alternatives to be involved at the same time.

The device for spacing adjustment preferably comprises a piston-cylinder arrangement. In an alternative the cylinder is rigidly connected to the proximal end of the optical lumen and the piston is rigidly connected to the proximal end of the optical strand. In another alternative the piston is rigidly connected to the proximal end of the optical lumen and the cylinder is rigidly connected to the proximal end of the optical strand. To achieve an adjustment in respect of that spacing, the piston can be fixed in different axial positions in the cylinder. For fixing purposes the arrangement can preferably have a clamping device, for example a clamping screw which is fitted into the cylinder wall with screwthreaded engagement and with which the piston is held fast in the cylinder in the desired axial position. That permits stepless spacing adjustment. It will be appreciated that it is also possible to provide for a stepped spacing adjustment, for example by clamping locations or fixing locations being provided on the piston or a piston rod, at given axial spacings.

The piston-cylinder arrangement with which spacing adjustment is effected and the length compensating device are preferably arranged in succession (one behind the other) between the proximal end of the optical strand and the proximal end of the optical lumen. That achieves optimum spacing adjustment in the axial direction of the optical strand and the catheter probe.

That spacing adjustment can be effected in particular when the length compensating movement of the length compensating device and the contact force, which is preset therewith, of the distal end of the optical strand against the cover, passes into the limit region. A reduction in the angle of view which results from the distal end of the optical strand coming loose from the cover can also be compensated or reversed by the change in spacing.

To improve the mechanical strength of the transparent cover and to improve the positioning of the transparent cover in the distal end of the optical lumen, there can be provided a holder which is glued into or fixedly anchored in the distal end of the optical lumen and which is fixed with a cylindrical peripheral surface to the inside of the distal end of the optical lumen, for receiving and positioning the transparent cover. In order to provide that the cover is satisfactorily anchored and fixed in position, the peripheral surface which in particular is of a circular-cylindrical configuration is provided with one or more recesses which are filled with an adhesive agent. A suitable adhesive agent is a hardenable adhesive which is introduced in liquid form into the recesses and between the cylindrical peripheral surface and the inside of the optical lumen and then hardened. The adhesive agent is preferably an epoxy resin-based compound. A holder of such a configuration for holding the cover forms an independent invention and is suitable for ensuring the mechanical stability of the cover and fixing of the cover in the distal end of the optical lumen.

That configuration provides for an improvement in the mechanical stability of the distal cover in the optical lumen and the arrangement and holding thereof. In that way force peaks which occur under some circumstances in the contact force with which the distal end of the optical strand bears against the cover can be effectively absorbed.

Advantageously the holder is of a sleeve-shaped configuration in the shape of a circular cylinder. At the distal end the sleeve can have an inwardly bent sleeve edge which is directed towards the axis of the sleeve. The cover bears against that sleeve edge which forms an inwardly disposed contact shoulder. It is also possible to form at the distal end of the sleeve an inwardly disposed contact shoulder against which the cover bears in a condition of being supported outwardly. The holder preferably comprises metal, in particular high-quality steel.

An opening which projects from the outside to the peripheral surface of the holder can be provided in the region of the axial extent of the holder in the material of the optical lumen, for the purposes of introducing the adhesive agent. The adhesive agent can be introduced through that opening in liquid form between the peripheral surface and the inside of the optical lumen and into the recesses in the peripheral surface and then hardened.

At least one optically operative component can be fixedly or interchangeably arranged in the holder. The optically operative component can have one or more optical lenses or can also consist of or include a video chip, the connecting wires of which are passed through the optical lumen. The connecting wires can be of a suitable configuration for positioning of the video chip or the video chip can be put into the distal position by means of a wire-shaped and spiral-shaped thrust element. The signals of the video chip can also be transmitted wirelessly using transponder technology. Optical fibers are then sufficient for illuminating the space to be observed.

In addition the optical strand or an additional optical fiber strand can be of such a design configuration that a stimulus radiation or stimulus light with which autofluorescence can be produced in biological cells or tissues can be transmitted therewith, in particular in early cancer detection. Suitable stimulus light sources and evaluation devices which are connected to the endoscope are known for example from DE 198 00 312 A1 and 101 16 859 A1.

Advantageously, an optical strand or optical strands of a uniform length can be provided for catheter probes involving differing lengths. In order to achieve length compensation in relation to the different catheter probes, an embodiment of the invention can provide protective casings of differing lengths. The parts of the optical strand, which project beyond the proximal end of the respective catheter probe, are passed through those protective casings. In that way it is possible to use an optical strand or optical strands of a uniform length for different purposes of use of the endoscope. For example catheter probe lengths of 20 cm, 30 cm, 60 cm, 85 cm and 185 cm length can be used. For shorter lengths of the catheter probes, it is possible to use an optical strand of reduced length. For example optical strands of 150 cm length and 300 cm length can be kept in readiness for the varying catheter probe lengths.

Preferably the optical strands are kept in readiness in tubular dispensers outside the catheter probe, wherein at its end the dispenser has a connection for a flushing device so that satisfactory cleaning and sterilisation of the optical strand in the dispenser is possible.

Preferably the invention is used in relation to an endoscope having a catheter probe whose distal end can be bent by means of a control element in different directions, optionally up to 180° and more. That control element extends along the catheter probe preferably in a control lumen of the catheter probe and is fixed to the distal end of the probe or in the proximity thereof and is actuated at the proximal end. An endoscope of that kind is known for example from DE 100 45 036 C1.

Figure 2:
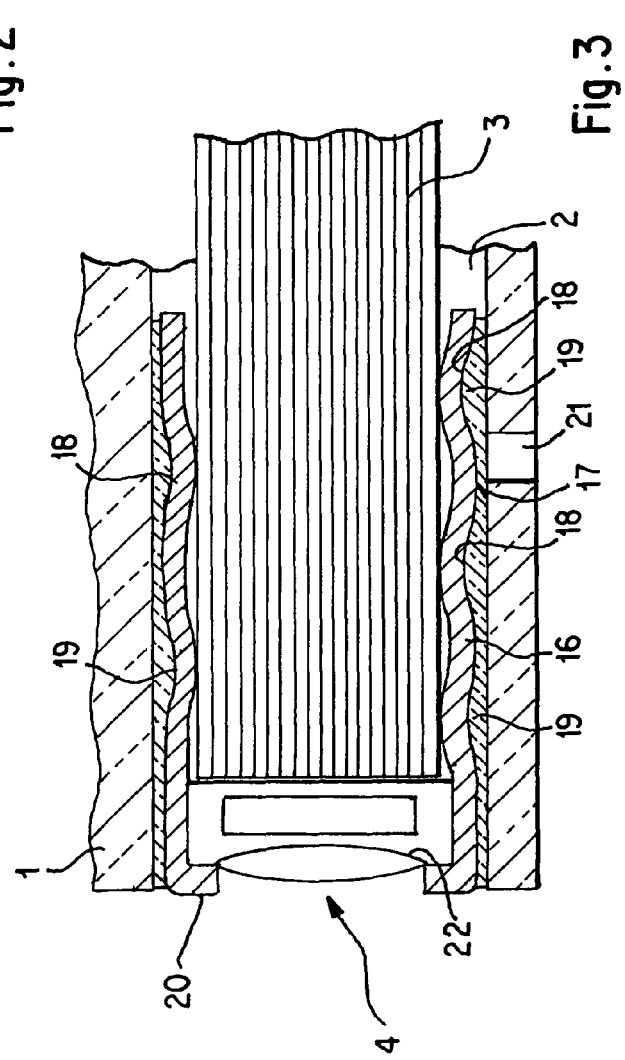
Figure 3:
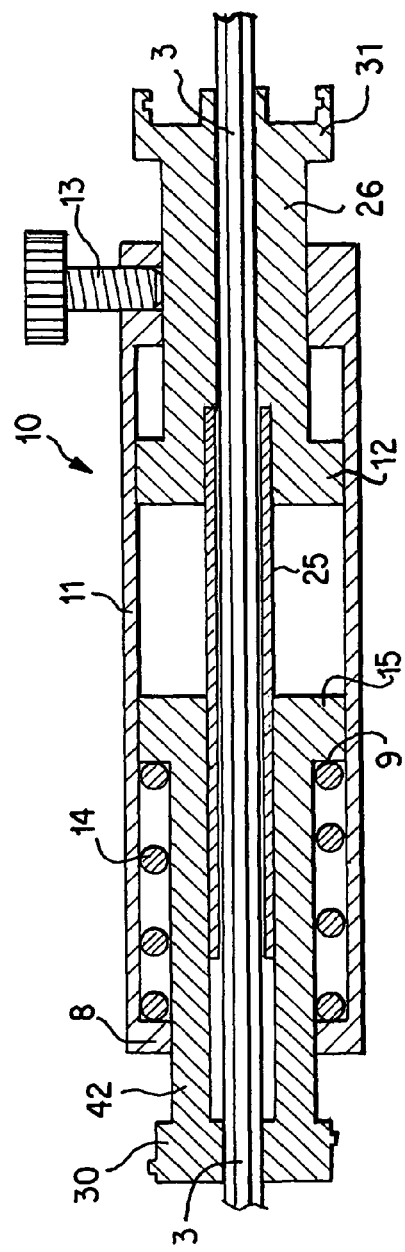
Figure 4:
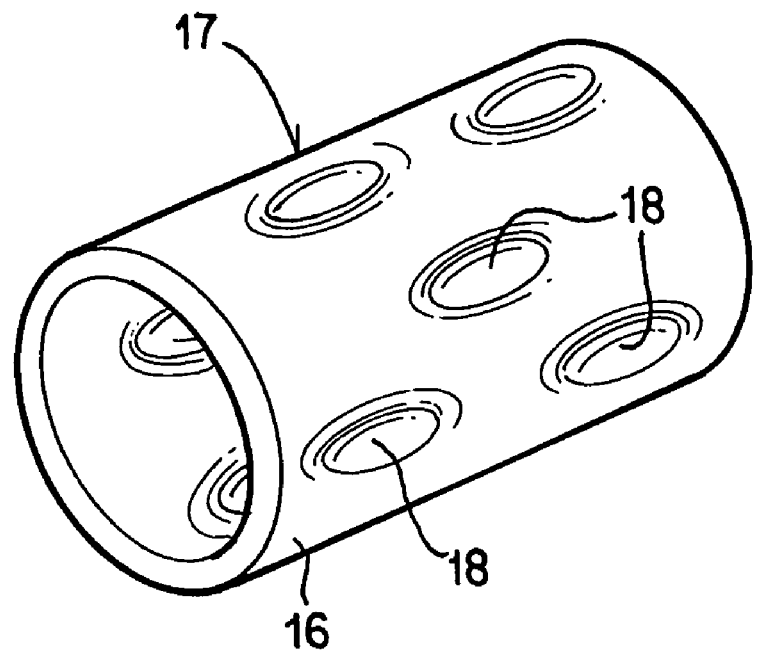
Figure 5:
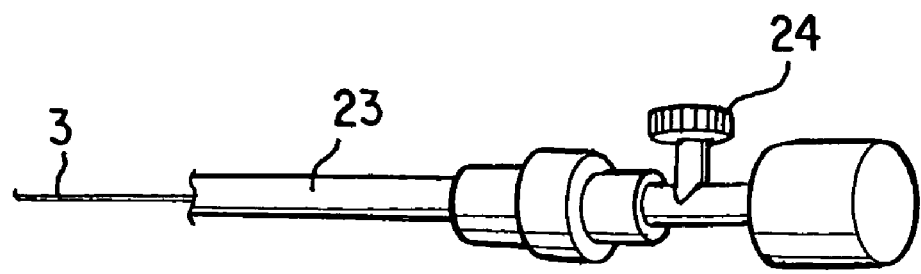

The invention is described is described in still greater detail by means of embodiments with reference to the Figures in which:

FIG. 1 is a diagrammatic view of an embodiment of the invention,

FIG. 2 is a sectional view through a length compensating device used in the embodiment of FIG. 1, FIG. 3 is a sectional view of the distal end of the catheter probe in the region of the optical lumen, FIG. 4 is a perspective view of a sleeve-shaped mounting means for a transparent cover closing the distal end of the optical lumen, and FIG. 5 shows an embodiment for a dispenser in which an optical strand used in the invention can be kept in readiness in a sterile condition.

The embodiment of an endoscope shown in FIG. 1 has a handle 27 which can also be of another known configuration and a catheter probe 1 which is to be releasably fixed thereto. The probe 1 is in the form of a multi-lumen probe and can have for example a working lumen or a plurality of working lumens for surgical instruments and at least one optical lumen 2 for an optical strand 3. It is also possible to provide separate optical lumens for the optical strand 3 which has an optical illumination means and an optical observation means. Separate lumens can likewise be provided in the probe 1 for flushing and suction removal purposes.

In addition the catheter probe 1 can have a control element, for example in the form of a pulling cable or pulling wire. As is known for example from DE 100 45 036 C1 the elongate control element is fixedly connected to a distal probe end 28 or is fixed in the proximity thereof and extends in the axial direction along the probe and is guided movably thereon. The distal end portion of the catheter probe 1 can be bent by the control element.

The distal probe end 28 which can be bent by means of the control element can be of the design configuration as is known from DE 201 18 886 U or from DE 199 28 272 A1.

The catheter probe 1 comprises a bendable material, in particular biocompatible plastic material. Preferably it is in the form of a disposable component which, after a surgical use, is released from the handle 27 and disposed of. In a fresh surgical intervention a new catheter probe which is kept in readiness as a disposable component in a sterile condition is fixed to the handle 27.

At the proximal end the catheter probe 1 has a probe attachment portion 33 comprising a rigid strong material. That material can also be a plastic material. Proximal lumen exits 34, 35, 36 and 37 are provided on the probe attachment portion 33. The control element is passed through the lumen exit 34. The lumen exit 35 is associated for example with a balloon lumen, the lumen exit 36 is associated for example with a working lumen and the lumen exit 37 is associated for example with the optical lumen 2. In known manner, the exits are equipped with coupling elements for forming connecting arrangements, for example for a bayonet fastening, a Luer lock or with similar coupling and connecting portions.

The catheter probe 1 can be connected non-rotatably to a rotary part of a rotary mounting 38 on the handle 27, in particular on the handle housing, by way of the rigid tubular lumen exit 34 for the control element 13. The catheter probe 1 can also be connected non-rotatably to the handle 27 or the probe attachment portion 33.

The optical strand 3 which includes optical illumination and observation means can be introduced into the optical lumen 2 of the catheter probe 1 through the lumen exit 37. Separate optical lumens can also be provided for the two strands of the optical illumination means and the optical observation means. The respective distal end of the optical lumen 5 is hermetically closed off by a transparent cover 4. That prevents contamination of the optical strand 3 at the target location. The remaining portion of the optical strand 3 is protected from contamination by the enclosing casing formed by the catheter probe 1. As will also be described hereinafter the optical strand 3 is displaced forwardly in the optical lumen 2 by means of a length compensating device 7 to the transparent cover 4 and is caused to bear thereagainst under a low contact pressure, for example about 2 N.

The optical strand 3 which projects beyond the proximal end of the catheter probe 1 and the lumen exit 37 is guided in the axial direction in a flexible tubular protective casing 39. The protective casing 39 forms protection from external influences. At the front (distal) end the protective casing 39 has a coupling portion which, with the proximal lumen exit 37, forms a releasable connecting device 29, for example a Luer lock. The rear (proximal) end of the casing is also equipped with a coupling element which can be releasably connected with a connection portion to the length compensating device 7, forming a releasable connecting device 30. The releasable connecting device 30 can be in the form of a Luer lock or the like.

The optical strand 3 is also guided through a length compensating device 7 which is to be described hereinafter and is fixed at its proximal optical strand end 6 to an adaptor 32. The corresponding light guide portion of the optical strand 3 can be connected to an illumination light source by way of an illumination connection 40 of the adaptor 32. In addition an ocular and/or camera system for detecting the items of image information communicated by the optical strand 3 can be connected to the adaptor 32. An ocular connection 41 on the adaptor 32 serves for that purpose.

The embodiment of the length compensating device 7 which is shown in FIG. 2 has a cylinder 11 which is preferably in the form of a gas cylinder. Provided in the cylinder is a piston 15 which is connected fixedly or integrally to the coupling portion of the connecting device 30 by way of a piston rod 42. In that way, by way of the protective casing 39 which is rigid in its longitudinal direction, the piston 15 is rigidly connected to the end 5 of the optical lumen, which is fixed to the connecting device 29. The end 5 of the optical lumen can also be provided for rigid connection to the piston 15, on the probe attachment portion 33.

At the end of the cylinder 11 which is at the left in FIG. 2, a support location is formed by an apertured end disk which is fixedly connected to the cylinder 11 and which can also be in one piece with the cylinder 11. That support location forms a force application location 8 for a spring 17 which is also supported against the piston 15 at a force application location 9. As already explained above, the force application location 9 is fixedly connected to the proximal end 5 of the optical lumen in the axial direction of the optical strand 3. The other force application location 8 at which the spring 14 in the form of a compression spring is supported is connected rigidly and fixedly to the proximal end 6 of the optical strand 3 in the axial direction thereof. That connection is effected by way of the cylinder 11 and a fixing device which is in the form of a clamping device 13 and with which the cylinder 11 is connected to a piston rod 26. The piston rod 26 is connected fixedly or integrally to a coupling portion of the connecting device 31. As can be seen from FIG. 1 the connecting device 31 connects the piston rod 26 fixedly to the adaptor 32 and thus the end 6 of the optical strand.

Arranged in the cylinder 11 is a further piston 12 which is connected to the piston rod 26 and which is guided movably in the axial direction when the clamping device 13 is released. The cylinder 11 and the displaceable piston 12 together with the releasable fixing device (clamping device 13) form a spacing adjusting device with which the spacing of the force application location 8 from the end 6 of the optical strand can be adjusted. For that purpose the clamping device 13 can be fixed in various axial positions on the piston rod 26 which is fixedly or integrally connected to the piston 12. In that situation at the same time the force application location 8 on the cylinder 11 is displaced in the axial direction, wherein moreover the respectively prevailing pressure force which is exerted by the spring 14 between the two force applications 8 and 9 on the cylinder 11 and on the piston 15 is altered. The pressure forces acting at the force application locations 8 and 9 provide that the distal end of the optical strand 3 is caused to bear against the transparent cover 4 under a given contact force. Upon bending of the catheter probe 1 during treatment and in particular upon bending of the distal end portion of the cathode probe 1, length compensation between the cathode probe 1 or the optical lumen 2 and the optical strand 3 is achieved to a certain extent by the compression spring and the displaceability of the piston 15 in the cylinder 11. Within that length compensation action, the arrangement ensures that the distal end of the optical strand bears against the cover 4. For that purpose the piston rod 42 and the piston 15 can be pulled out of the cylinder 11 by a given amount in FIG. 2 so that the desired pressure force is exerted by the spring 14. When considerable bending effects are involved or also when the catheter probe 1 is guided in an outer catheter tube, it can happen, particularly when a long catheter length is involved, that the desired length compensating effect no longer takes place and the distal end of the optical strand 3 is pressed against the cover 4 with an excessive high force or, in the opposite direction, the distal end of the optical strand 3 comes away from the cover 4. In order to prevent that, the arrangement has the above-discussed spacing adjusting device formed by the additional piston 12 in the cylinder 11. That spacing adjusting device is thus also formed by a piston-cylinder arrangement 10 which, in the form of the clamping device 13, also has a fixing device for fixing the piston 12 in various axial positions within the cylinder 11. As already discussed above, the piston 12 is connected rigidly to the proximal end 6 of the optical strand by way of the piston rod 26 and the connecting device 31.

As can be seen from FIG. 2 the optical strand 3 is guided in the axial direction through the length compensating device 7 so that the pistons 12 and 15 are movable with respect to the optical strand 3. For the purposes of axial alignment, a guide tube 25 can be provided on the piston 12; the guide tube 25 projects displaceably into the piston 15. It will be appreciated that it is also possible to fix the guide tube 25 to the piston 15 and to support it displaceably in the piston 12.

The length compensating device 7 acts in the same manner when the piston 12 and its piston rod 26 are rigidly connected to the end 5 of the optical lumen and the piston 15 with its piston rod 42 is rigidly connected to the end 6 of the optical strand. For that purpose it is only necessary for the coupling element connected to the piston rod 42 to be connected to the coupling element of the adaptor 32 and for the coupling element connected to the piston rod 26 to be connected to the coupling element at the proximal end of the protective casing 39.

FIGS. 3 and 4 show a fastening device in the form of a sleeve-shaped holder 16 for the transparent cover 4. That holder is fastened in the distal end region of the optical lumen 2 by means of an adhesive 19 arranged between the inside of the optical lumen 2 and the outwardly disposed cylindrical peripheral surface 17. The adhesive agent 19 can be a hardenable adhesive agent, for example epoxy resin-based, which can be introduced through an opening 21 in liquid form. The opening 21 extends from the outside of the catheter probe 1 as far as the peripheral surface 17 of the holder 16. Recesses 18 are also provided in the peripheral surface 17, for example in the form of impressions therein. The adhesive agent introduced also fills those recesses 18. That affords an increase in the adhesion of the cover 16 at the inside of the optical lumen 2, in relation to forces acting in the axial direction.

Provided at the distal end of the sleeve-shaped holder 16 is a peripherally extending edge 20 which is directed inwardly towards the axis of the lumen and against which the cover 4 bears and is supported outwardly. The plurality of recesses 18 which are disposed at separate locations are provided in the peripheral surface 17, as can be seen for example from FIG. 4. It is also possible to provide peripherally extending recesses in the peripheral surface 17. The recesses can be produced in the form of impressions involving deformation of material or also by the removal of material from the peripheral surface 17.

Together with the cover 4 or in the cover 4, an optically operative component 22 or a plurality of optically operative components can be arranged in the holder 16. The holder can also be formed by the optically operative component 22. The holder can be of an optically neutral nature, in which case an optically operative component can be provided at the distal end of the optical strand 3. The optically operative component can have one or more optical lenses.

A video chip can also be used as the optically operative component. The video chip converts the detected image into corresponding image signals which are fed by way of connecting wires guided through the optical lumen 2, to an evaluation device at the proximal end of the catheter probe. The video chip can be fixedly installed and can form a component part of the cover 4. Preferably however the video chip is interchangeably inserted into the optical lumen 2 and is pressed against the sleeve edge 20 which acts as a brake. Instead of galvanic transmission of the signals from the video chip, they can also be transmitted by telemetric means using transponder technology. In that case the optical strand 3 only still needs optical fibers for illumination of the space to be observed. That optical strand can also be arranged in a separate optical lumen.

Suitably dimensioning the lengths of various protective casings 39 means that it is possible to compensate for differing lengths of the catheter probe 1, with the length of the optical strand 3 remaining the same. By way of example, with two optical strand lengths of 150 cm and 300 cm, it is sufficient for catheter lengths of between 20 cm and 185 cm to be covered by means of the differing lengths of the protective casing 39.

FIG. 5 shows an end of an optical dispenser 23 in which the optical strand 3 can be kept in readiness under sterile conditions. The end of the optical dispenser 23 has a connection 24 for a flushing device. In that way it is possible to flush the optical strand 3 in the dispenser 23 and thus possibly sterilise it or disinfect it. After the disinfecting operation the optical dispenser 23 can be flushed with water and then dried with compressed air. The connection to the items of equipment which are respectively required for those operations can be made by way of the connection 24.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed:

1. An endoscope comprising a flexible catheter probe having a plurality of lumens, at least one optical lumen in which there is provided an optical strand with optical fibers extending in the longitudinal direction of the catheter, a transparent cover which at least partially closes a distal opening of the optical lumen, and a length compensating device which is configured to act resiliently between a proximal end of the optical lumen and a proximal end of the optical strand and with which a distal end of the optical strand is held in contact against the transparent cover,
   wherein spacing of a force application location of the length compensating device, which location is rigidly connected to the proximal end of the optical strand, from the proximal end of the optical strand or the spacing of a force application location of the length compensating device, which location is rigidly connected to the proximal end of the optical lumen, from the proximal end of the optical lumen, is adjustable,
   wherein the length compensating device includes a piston-cylinder arrangement comprising a cylinder in which two pistons are arranged, one of the two pistons being rigidly connected to the proximal end of the optical lumen and the other of the two pistons being rigidly connected to the proximal end of the optical strand such that the one of the two pistons can be fixed by a clamping device in the cylinder at selected axial positions, and the force application location is located between the other of the two pistons and the cylinder.

2. An endoscope as set forth in claim 1, wherein the spacing-adjusting piston-cylinder arrangement and the length compensating device are arranged in succession between the proximal end of the optical strand and the proximal end of the optical lumen.

3. An endoscope as set forth in claim 1, wherein the length compensating device and the spacing-adjusting piston-cylinder arrangement are arranged in a common cylinder.

4. An endoscope as set forth in claim 1, wherein the length compensating device has a spring which is operative between a piston rigidly connected to the proximal end of the optical lumen or the proximal end of the optical strand, and the cylinder which is rigidly connected to the proximal end of the optical strand or the proximal end of the optical lumen.

5. An endoscope as set forth in claim 4, wherein the spring is in the form of a compression spring.

6. An endoscope as set forth in claim 4, wherein the length compensating device has in the common cylinder two pistons of which the one piston is for spacing adjustment and the other piston is acted upon by the force of the compression spring and that the optical strand is guided in the axial direction through the two pistons.

7. An endoscope as set forth in claim 1, wherein the optical strand is guided in the cylinder at least partially in a preferably axially arranged guide tube.

8. An endoscope as set forth in claim 7, wherein the guide tube is fixedly connected to the proximal end of the optical strand or the proximal end of the optical lumen.

9. An endoscope as set forth in claim 1, wherein the optical strand is suitable for passing a radiation, in particular light at a wavelength by which autofluorescence of body tissue or body cells to be investigated is stimulated.

10. An endoscope as set forth in claim 1, wherein an optical strand of uniform length is provided for catheter probes of different lengths, wherein there are to be arranged between the proximal end of the catheter probe and the length compensating device, respective protective casings of differing lengths, which compensate for the differing lengths of the catheter probes and through which is guided the part of the optical strand, which projects beyond the proximal end of the catheter probe.

11. An endoscope as set forth in claim 1, wherein a tubular optical dispenser is provided outside the catheter probe for supplying the optical strand, a connection for a flushing device being provided at one end of the optical dispenser.

12. An endoscope as set forth in claim 1, wherein the catheter probe has a control element which is actuable at its proximal end and which is fixed at the distal end of the probe or in the proximity thereof for bending the end of the probe and is guided movably in the axial direction on the probe, in particular in a control lumen of the catheter probe.

* * * * *